United States Patent [19]
Albrecht et al.

[11] Patent Number: 4,610,817
[45] Date of Patent: Sep. 9, 1986

[54] N-ACYL DERIVATIVES OF PEPTIDES, THEIR PREPARATION AND THEIR USE IN THE TREATMENT OF DISORDERS, AND AGENTS FOR THIS PURPOSE

[75] Inventors: Hans P. Albrecht, Weinheim; Horst Kreiskott, Wachenheim, both of Fed. Rep. of Germany

[73] Assignee: BASF Aktiengesellschaft, Ludwigshafen, Fed. Rep. of Germany

[21] Appl. No.: 513,023

[22] Filed: Jul. 12, 1983

[51] Int. Cl.$^4$ .................. A61K 37/02; C07K 5/02
[52] U.S. Cl. .......................... 514/2; 514/19; 260/998.2
[58] Field of Search .............. 260/112.5; 424/177; 514/2

[56] References Cited

U.S. PATENT DOCUMENTS 4,018,912  4/1977  Failli et al. ............... 424/177
4,278,595  7/1981  Cort ....................... 260/112.5 R

OTHER PUBLICATIONS

Englehardt et al., "Antiparkinsonism Drugs" in *Medicinal Chemistry*, 3rd ed, Part II, 1970, pp. 1538–1543.
The Merck Index, 9th Edition, 1976, p. 805.
Acta Pharmaceutica Suecica, vol. 13, No. 4, 1976, pp. 289–299.
Journal of Medicinal Chemistry, vol. 21, No. 2, 1978, pp. 165–169.

*Primary Examiner*—Donald B. Moyer
*Assistant Examiner*—Jacqueline M. Stone
*Attorney, Agent, or Firm*—Keil & Weinkauf

[57] ABSTRACT

Novel N-acyl derivatives of peptides related to L-pro-L-leu-gly-NH$_2$, melanocyte stimulating hormone-release inhibiting factor (MIF), and therapeutic compositions which are useful for the treatment of depression.

6 Claims, No Drawings

N-ACYL DERIVATIVES OF PEPTIDES, THEIR PREPARATION AND THEIR USE IN THE TREATMENT OF DISORDERS, AND AGENTS FOR THIS PURPOSE

The present invention relates to novel N-acyl derivatives of peptides, processes for their preparation, drugs which contain these novel compounds and their use in the treatment of disorders.

The tripeptide L-Pro-L-Leu-Gly-NH$_2$ (MIF) is the melanocyte stimulating hormone-release inhibiting factor (The Merck Index, 9th Edition, 1976). In addition to its endocrinal action, the tripeptide has a neurotransmitter or neuromodulator effect in the central nervous system. Clinical studies have shown that MIF alone or in combination with L-dopa has an advantageous effect on tremor, rigor and akinesia in Parkinson patients (A. J. Kastin and A. Barbeau, Can. Med. Assoc. J. 107, (1972), 1097 and F. Gerstenbrand et al., Wien. klin. Wschr. 87, (1975), 822).

However, wide therapeutic use of this tripeptide is hindered by the lack of sufficient oral activity and the short duration of action.

Attempts have also been made to prepare, by means of molecular transformation in which the pharmacological activity of H-Pro-Leu-Gly-NH$_2$ is retained, compounds which have oral activity and an adequate duration of action.

Efforts have been concentrated on exchanging the central L-leucine for D-leucine (U.S. Pat. No. 4,278,595) or for an N-alkyl derivative of L- or D-leucine (German Laid-Open Application DOS No. 2,633,976).

The replacement of the L-proline by an acid or amino acid has been little investigated to date, since, apart from exchange for L-pyroglutamic acid, which does not have an adverse effect (S. Björkman et al., Acta. Pharm. Suec. 13, (1976) 289), the products obtained are pharmacologically inactive (R. C. Johnson et al., J. Med. Chem. 21, (1978) 165).

We have found that N-acyl derivatives of peptides of the formula I $$X-NH-CR^2R^3-CO-NH-CH_2-CO-R^1, \quad I$$

where R$^1$ is C$_1$–C$_5$-alkoxy or an amino radical of the formula NR$^4$R$^5$, where R$^4$ and R$^5$ are identical or different and are each hydrogen or C$_1$–C$_5$-alkyl, R$^2$ and R$^3$ are identical or different and are each C$_1$–C$_5$-alkyl, phenyl, benzyl or naphthyl or, together with the carbon atom which they share, may furthermore form an aliphatic ring system of 3 to 7 carbon atoms or a 1,1- or 2,2-indanediyl radical, and X is pyrrol-2-ylcarbonyl, indol-2-ylcarbonyl, cyclopentylcarbonyl, L-pyrrolidin-2-ylcarbonyl, L-4,5-dehydropyrrolidin-2-ylcarbonyl, L-5-oxopyrrolidin-2-ylcarbonyl, L-1,3-thiazolidin-4-ylcarbonyl or L-1,4-thiazan-2-ylcarbonyl, and their salts with physiologically tolerated acids exhibit very good actions on the central nervous system.

In formula I, R$^1$ is preferably NR$^4$R$^5$.

Physiologically tolerated acids which are particularly useful for salt formation are hydrochloric acid, sulfuric acid, phosphoric acid, acetic acid, lactic acid, succinic acid, fumaric acid and malic acid.

Where R$^2$ and R$^3$ are different, the starting materials of the formula H$_2$N—CR$^2$R$^3$—COOH occur as racemates. They can be separated into their antipodes by a conventional method, and employed in the reaction in the form of pure D- or L-compounds.

If X-OH is an optically active amino acid, it is also possible to use the starting materials of the formula H$_2$N—CR$^2$R$^3$—COOH in the reaction sequence in the form of their racemates. Mixtures of two diastereomeric peptides are then obtained, and these mixtures can be separated by chromatography or crystallization.

To prepare the novel compounds, the starting substances X—OH, H$_2$N—CR$^2$R$^3$—COOH and H$_2$N—CH$_2$—CO—R$^1$, where X, R$^1$, R$^2$ and R$^3$ have the above meanings, are condensed with one another by a method conventionally used in peptide chemistry.

The synthesis can be carried out as follows: first X—H is condensed with H$_2$N—CR$^2$R$^3$—COOH and then the resulting compound is reacted with H$_2$N—CH$_2$—CO—R$^1$, or first H$_2$N—CR$^2$R$^3$—COOH is condensed with H$_2$N—CH$_2$—CO—R$^1$ and the peptide formed is reacted with X-OH. The individual reaction stages are carried out after the amine and acid functions not participating in the particular stage have been blocked by means of suitable protective groups. When the reaction is complete, the protective groups are split off by a method conventionally used in peptide chemistry. Such methods are described in detail in Methoden der organischen Chemie, volumes XV/1 and XV/2, editor: E. Müller, Georg-Thieme-Verlag, Stuttgart, 1974.

The following synthetic route has proved particularly advantageous for the preparation of the novel compounds: the carboxylic acid X—OH, in which any NH group present is protected by means of a benzyloxycarbonyl or butoxycarbonyl group, is reacted with an amino acid ester of the formula II $$H_2N-CR^2R^3-CO-OR^6 \quad (II)$$

where R$^6$ is methyl or ethyl, to give an intermediate of the formula III $$X-NH-CR^2R^3-CO-OR^6 \quad (III)$$

To do this, it is generally necessary to activate the free acid function of the carboxylic acid X—OH before it acts on the amino acid derivative II. Activated derivatives of carboxylic acids are preferably the mixed anhydrides, which are prepared in situ in the presence of an alkyl chloroformate, e.g. isobutyl chloroformate or ethyl chloroformate, as well as adducts on carbodiimides, preferably dicyclohexylcarbodiimide, or activated esters, preferably the N-hydroxysuccinimide esters which, if appropriate, can be prepared in situ from N-hydroxysuccinimide and dicyclohexylcarbodiimide. The condensation of the activated derivative is carried out in an organic solvent, e.g. dioxane, tetrahydrofuran, dichloromethane, chloroform, toluene or dimethylformamide, or in an aqueous organic medium in the presence of a base. Preferred bases are triethylamine, N-methylmorpholine and sodium bicarbonate. The reaction temperature is from −10 to +30°C. and the reaction time is from 3 hours to 4 days.

The ester group of the compound III is cleaved hydrolytically in water or in an aqueous organic medium by treatment with an equivalent amount of dilute alkali at from 0° to 40° C. for from 1 hour to 2 days. After acidification and the appropriate working up procedure, the carboxylic acid IV is obtained:

$$X-NH-CR^2R^3-CO-OH \quad IV.$$

This is reacted with a glycine derivative of the formula V

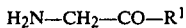
$$H_2N-CH_2-CO-R^1 \qquad V.$$

In this reaction, it is generally necessary to activate the free acid function of the carboxylic acid IV before it acts on the glycine derivative. This activation is effected in the above manner, by formation of a mixed anhydride, a carbodiimide adduct or an activated ester.

The novel compounds of the formula I, in which X does not contain nitrogen, are obtained in this manner. If X contains a nitrogen atom, it is also necessary to split off the protective group. Where the latter is benzyloxycarbonyl, this is advantageously split off by hydrogenation in the presence of a noble metal catalyst in an inert solvent at room temperature. Preferred noble metal catalysts are palladium, platinum or Raney nickel. In a preferred embodiment, for example, 10% strength palladium on carbon is used. Preferred solvents are methanol, ethyl acetate and glacial acetic acid. Where the protective group is t-butoxycarbonyl, this is advantageously split off by treatment with an excess of trifluoroacetic acid or with a solution of hydrogen chloride in an inert organic solvent, e.g. ethyl acetate, dioxane or tetrahydrofuran. The cleavage reaction is carried out at from 0° to 20° C. for from 5 to 30 minutes.

The novel N-acyl derivatives of dipeptides are substantially stable to the action of proteolytic enzymes, are active after oral administration, and have a long duration of action.

The superiority of the novel substances is shown, in particular, in the following test models:

1. In accordance with G. M. Everett (in Antidepressant Drugs, edited by S. Garattini and M. N. G. Dukes, Amsterdam 1967, pages 164 et seq.), an L-dopa/pargyline combination which causes a weak pattern of excitation is administered to mice. A pronounced pattern of excitation develops only as a result of pretreatment with substances which stimulate the central nervous system. In this test model, the novel tripeptides are effective when administered orally in doses of 0.02 mg/kg and more.

2. In addition to peripheral symptoms, centrally induced scratching results when the cholinomimetic pilocarpine is administered to rats (H. Kreiskott, Arch. exp. Path. Pharmak. 247 (1964), 317); this scratching can be prevented by means of central anticholinergics or central monaminergic stimulants (H. Kreiskott and H. P. Hofmann, 6th Int. Congress Pharmacol., Helsinki 1975, Abstr. 825). Oral pretreatment with the novel tripeptides suppresses the centrally induced scratching due to pilocarpine.

3. The action pattern and toxicity pattern of the substances effective in test models 1 and 2 were additionally tested on the mouse. The symptoms were detected and quantified by the method due to Irwin (Psychopharmakologia 13 (1968), 222). The various test parameters are measured shortly before administration of the substance as well as ½, 1, 2, 3 and 24 hours after oral administration. Each dose was administered to a group of 3 animals, and the first test of behavior was carried out after allowing the animals 30 minutes to become accustomed to the macrolon cage. Basic behavior, central stimulation and depression as well as autonomic symptoms are measured. In particular, these are:

posture
position of limbs
cleaning behavior
stupor
spontaneous and induced locomotor activity
respiration
sensomotor reactions (reflexes)
width of palpebral fissure
pupil size and
body temperature, etc.

The novel substances produce higher locomotor activity as well as increased sniffing, standing up and cleaning. These symptoms occur to an equal extent both in the case of dopaminergic substances and in the case of dopamine-stimulating substances.

Accordingly, the novel substances clearly stimulate dopaminergic processes. In test model 1 (L-dopa potentiation), the action of exogenic dopamine is increased, while in 2 (pilocarpine stimulation) and 3 (action pattern) the effect of the endogenic dopamine is reinforced.

4. Rats pretreated subcutaneously with average doses of morphine do not show any striking features in their overall behavior. However, if an additional external stimulus, such as placing a clip on the tail, is applied, the animals abruptly become rigid and exhibit catalepsy. When the stimulus is removed, the rats again behave normally (G. Stille, Zur Pharmakologie katatonigener Stoffe, Aulendorf 1971, page 30). This stimulus-induced condition can be prevented by means of an intravenous injection of the claimed tripeptides.

The novel peptides, either alone or in combination with L-dopa, are therefore useful for the oral therapy of depressions. They can also be employed for preventing or treating opiate dependence.

The novel compounds can be administered in a conventional manner, either orally or parenterally (subcutaneously, intravenously, intramuscularly or intraperitoneally). They may also be administered through the nasopharyngeal space by means of vapors or sprays.

The dose depends on the age, condition and weight of the patient and on the route of administration. As a rule, the daily dose of active compound is from about 0.1 to 100 mg/kg of body weight when administered orally, and from about 0.01 to 10 mg/kg of body weight when administered parenterally.

The novel compounds can be used in the conventional solid or liquid pharmaceutical forms, for example tablets, film tablets, capsules, powders, granules, coated tablets, suppositories, solutions or sprays. These are prepared in a conventional manner, and to do so the active compounds can be mixed with the conventional pharmaceutical auxiliaries, such as tablet binders, fillers, preservatives, tablet disintegrators, flow regulators, softeners, wetting agents, dispersants, emulsifiers, solvents, retarding agents, antioxidants and/or propellants (cf. H. Sucker et al., Pharmazeutische Technologie, Thieme-Verlag, Stuttgart, 1978). The resulting forms for administration usually contain the active compound in an amount of from 0.1 to 99% by weight.

Experimental section

The Examples which follow illustrate the invention without restricting it.

All the reactions were monitored by means of thin-layer chromatography on $F_{254}$ precoated silica gel plates from Merck. Depending on the polarity of the compounds investigated, the mobile phase used was dichloromethane/ acetone (from 20:1 to 5:1), dichloromethane/methanol (from 20:1 to 2:1) or butanol/ethyl acetate/glacial acetic acid/ water (4:1:1:1).

The novel compounds obtained in the Examples below are pure according to thin-layer chromatography.

The NMR spectra are in agreement with the structure given.

Celit ® is a filtration assistant from Johns-Manville.

Preparation of D- or L-2-methylleucine methyl ester 220.0 g of L(+)-tartaric acid were added to a stirred solution of 233.0 g of D,L-2-methylleucine methyl ester in 1170 ml of methanol. Precipitation of the tartrate of L-2-methylleucine methyl ester began after a short time, and was completed by keeping the mixture at 5°C. overnight. The precipitate was filtered off, washed with a little methanol and partitioned between 1500 ml of chloroform and 500 ml of 10% strength sodium carbonate solution. The aqueous phase was extracted twice with chloroform, and the combined extracts were washed 3 times with 100 ml of water, dried over sodium sulfate and evaporated down under reduced pressure. Yield: 78 g (34%) of L-2-methylleucine methyl ester, $[\alpha]_D^{20} = +20°$ C. (c=1.0, dichloromethane).

130 g of the base were liberated from the mother liquor of the tartrate of L-2-methylleucine methyl ester by a method similar to that described above. 122 g of D(−)-tartaric acid were added to this base in methanol, and the tartrate of D-2-methylleucine methyl ester was precipitated. This was converted, as described above, to 68 g (31%) of D-2-methylleucine methyl ester, $[\alpha]_D^{20} = -21°$ (c=1.0, dichloromethane).

EXAMPLE 1a

Pyrrol-2-ylcarbonyl-L-2-methylleucyl-glycinamide 23.0 g of dicyclohexylcarbodiimide and 16.0 g of L-2-methylleucine methyl ester were added to 11.1 g of pyrrole-2-carboxylic acid in 200 ml of dioxane at 10°C., and the reaction mixture was stirred for 2 hours at 10°C. and then for 24 hours at room temperature. The dicyclohexylurea formed was filtered off, the filtrate was evaporated down under reduced pressure, the residue was taken up in ethyl acetate and the solution was washed successively with 10% strength aqueous citric acid solution, sodium carbonate solution and water, dried over sodium sulfate and evaporated down under reduced pressure. After purification by chromatography over a silica gel column (elution with a 10:1 mixture of dichloromethane and ethyl acetate), 7.5 g of pyrrol-2-ylcarbonyl-L-2-methylleucine methyl ester were obtained.

6.4 g of this product in 100 ml of a 4:1 mixture of dioxane and water were mixed with 13 ml of 1N sodium hydroxide solution at room temperature. After 24 hours, the major part of the dioxane was evaporated off under reduced pressure, 50 ml of water were added to the residue, the mixture was extracted several times with ethyl acetate, the aqueous phase was brought to pH 2-3 by the addition of citric acid and the resulting carboxylic acid was extracted with ethyl acetate. The extract was washed with a little water, dried over sodium sulfate and evaporated down under reduced pressure to give 6.0 g of pyrrol-2-ylcarbonyl- L-2-methyl-leucine.

This was dissolved in 50 ml of dimethylformamide and 2.8 ml of triethylamine, and 2.7 ml of isobutyl chloroformate were added dropwise to the stirred solution at −10° C. After 15 minutes, 3.3 g of glycinamide hydrochloride in 10 ml of dimethylformamide and 4.2 ml of triethylamine were added to the resulting solution of the asymmetric acid anhydride, and the mixture was stirred for 1 hour at −10°C. and then for 48 hours at room temperature, after which it was evaporated down under reduced pressure. The residue was taken up in ethyl acetate, and the organic phase was washed successively with 10% strength aqueous citric acid solution, sodium carbonate solution and water, dried over sodium sulfate and evaporated down under reduced pressure. Chromatography of the residue over a silica gel column (elution with a 5:1 mixture of dichloromethane and methanol) gave 3.3 g (56%) of pyrrol-2-ylcarbonyl-L-2-methylleucyl-glycinamide of melting point 113°–128° C. (dichloromethane/ether), $[\alpha]_D^{20} = +3°$ (c=0.5, methanol).

The following compounds were obtained by a similar method:

1b. Pyrrol-2-ylcarbonyl-D-2-methylleucyl-glycinamide (48%), mp.=95°–125° C. (dichloromethane/ether), $[\alpha]_D^{20} = -4°$ (c=0.5, methanol);

2a. Cyclopentylcarbonyl-L-2-methylleucyl-glycinamide (59%), mp.=125°–131° C. (isopropanol/ether), $[\alpha]_D^{20} = -12°$ (c=0.5, methanol);

2b. Cyclopentylcarbonyl-D-2-methylleucyl-glycinamide (49%), mp.=124°–130° C. (isopropanol/ether), $[\alpha]_D^° = +11°$ (c=0.5, methanol);

3a. Indol-2-ylcarbonyl-L-2-methylleucyl-glycinamide (37%), mp.=130°–140° C. (dichloromethane/ether/hexane), $[\alpha]_D^° +11°$ (c=0.5, methanol);

3b. Indol-2-ylcarbonyl-D-2-methylleucyl-glycinamide (45%), mp.=120°–135° C. (dichloromethane/ether/hexane), $[\alpha]_D^° = -14°$ (c=0.5, methanol).

EXAMPLE 4a

L-Prolyl-L-2-methylleucyl-glycinamide 7.3 ml of isobutyl chloroformate were added dropwise to 13.7 g of N-benzyloxycarbonyl-L-proline and 7.7 ml of triethylamine in 90 ml of dimethylformamide at −10° C. After 15 minutes, 8.8 g of L-2-methylleucine methyl ester were added to the resulting solution of the asymmetric acid anhydride, and the reaction mixture was stirred for 1 hour at −10° C. and then for 16 hours at room temperature, after which it was taken up in ethyl acetate. The organic phase was washed successively with 10% strength aqueous citric acid solution, sodium carbonate solution and water, dried over sodium sulfate and evaporated down under reduced pressure to give 20.6 g of N-benzyloxycarbonyl-L-prolyl-L-2-methylleucine methyl ester.

This was dissolved in 250 ml of a 4:1 dioxane/water mixture at room temperature, and the stirred solution was hydrolyzed with 55 ml of 1N sodium hydroxide solution added in 1 ml portions, the consumption of alkali being monitored by means of thymolphthalein as an indicator. After acidification with an equivalent amount of hydrochloric acid, the major part of the dioxane was distilled off under reduced pressure, the residue was taken up in ethyl acetate and the solution was extracted with dilute potassium bicarbonate solution. The aqueous extracts were acidified and then extracted several times with ethyl acetate. The combined extracts were washed with a little water, dried over sodium sulfate and evaporated down under reduced pressure to give 13.6 g of N-benzyloxycarbonyl-L-prolyl-L-2-methylleucine.

3.9 ml of isobutyl chloroformate were added dropwise to 11.3 g of N-benzyloxycarbonyl-L-prolyl-L-2- methylleucine and 4.5 ml of triethylamine in 50 ml of dimethylformamide at −10° C., while stirring. After 15 minutes at this temperature, 3.6 g of glycinamide hydrochloride and 4.6 ml of triethylamine were added to the resulting solution of the asymmetric acid anhydride, and the mixture was stirred for 1 hour at −10° C. and then for 48 hours at room temperature, after which it was evaporated down under reduced pressure. The residue was taken up in ethyl acetate, and the organic phase was washed successively with 10% strength aqueous citric acid solution, sodium carbonate solution and water, dried over sodium sulfate and evaporated down under reduced pressure. The residue was purified by chromatography over a silica gel column (elution with a 5:1 mixture of dichloromethane and methanol), and 6.6 g of N-benzyloxycarbonyl-L-prolyl-L-2-methylleucyl-glycinamide were obtained.

4.6 g of this compound were dissolved in 150 ml of methanol, and the solution was hydrogenated in the presence of 0.5 g of palladium on carbon (10%). The mixture was filtered over Celit ® and the filtrate was then evaporated down under reduced pressure. Trituration with ether gave 2.7 g of crystals of L-prolyl-L-2-methylleucyl-glycinamide of melting point 128°–132° C. (ether), $[\alpha]_D^{20} = -33°$ (c=0.5, methanol).

The following compounds were obtained by a similar method:

4b. L-Prolyl-D-2-methylleucyl-glycinamide (35%), mp.=155°–160° C. (ether/hexane), $[\alpha]_D^{20} = -37°$ (c=0.5, methanol);

5a. L-Pyroglutamyl-L-2-methylleucyl-glycinamide (23%), mp.=188°–191° C. (methanol/ether), $[\alpha]_D^{20} = -4°$ (c=0.5, methanol);

5b. L-pyroglutamyl-D-2-methylleucyl-glycinamide (23%), mp.=202°–204° C. (dichloromethane/ether), $[\alpha]_D^{20} = -25°$ (c=0.5, methanol).

EXAMPLE 6a 4,5-Dehydro-L-prolyl-L-2-methylleucyl-glycinamide

In a reaction sequence similar to that described in Example 4a, N-butoxycarbonyl-4,5-dehydro-L-proline gave N-butoxycarbonyl-4,5-dehydro-L-prolyl-L-2-methylleucyl-glycinamide. The protective group was split off by the following procedure: 0.8 g of the butoxycarbonyl compound was treated with 15 ml of 6N hydrogen chloride in dioxane for 10 minutes at room temperature, after which the mixture was evaporated down under reduced pressure, the residue was co-evaporated several times with toluene and the final residue was crystallized from isopropanol/ether. 0.5 g of 4,5-dehydro-L-prolyl-L-2-methylleucyl-glycinamide of melting point 137°–153° C. (isopropanol/ether) was obtained.

The following compounds were obtained by a similar method:

6b. 4,5-Dehydro-L-prolyl-D-2-methylleucyl-glycinamide (27%), $[\alpha]_D^{20} = -15°$ (c=0.5, methanol);

7a. L-1,3-Thiazolidin-4-ylcarbonyl-L-2-methylleucyl-glycinamide hydrochloride, mp.=155°–165° C. (methanol/ether), $[\alpha]_D^{20} = -61°$ (c=0.5, methanol);

7b. L-1,3-Thiazolidin-4-ylcarbonyl-D-2-methylleucyl-glycinamide hydrochloride, mp.=190°–200° C. (methanol/ether), $[\alpha]_D^{20} = -50°$ (c=0.5, methanol);.

8a. L-1,4-Thiazan-3-ylcarbonyl-L-2-methylleucyl-glycinamide hydrochloride, mp.=184°–188° C. (methanol/ether), $[\alpha]_D^{20} = +13°$ (c=0.5, methanol);

8b. L-1,4-Thiazan-3-ylcarbonyl-D-2-methylleucyl-glycinamide hydrochloride, mp.=176°–181° C. (methanol/ether), $[\alpha]_D^{20} = +2°$ (c=0.5, methanol).

EXAMPLE 9

L-Prolyl-1-aminocyclopent-1-ylcarbonyl-glycinamide 5.4 ml of triethylamine and 13.5 g of the N-hydroxysuccinimide ester of N-benzyloxycarbonyl-L-proline were added to 5.6 g of methyl 1-aminocyclopentane-1-carboxylate in 50 ml of dioxane at 10° C., the reaction mixture was stirred for 2 hours at this temperature, 20 ml of water were then added and the reaction was allowed to continue for 20 hours at room temperature. The mixture was taken up in ethyl acetate, and the organic phase was washed successively with 10% strength aqueous citric acid solution, sodium carbonate solution and water, dried over sodium sulfate and evaporated down under reduced pressure. Crystallization of the solid residue gave 11.5 g (79%) of methyl N-benzyloxy-carbonyl-L-prolyl-1-aminocyclopentane-1-carboxylate.

8.2 g of the methyl ester thus obtained were dissolved in 100 ml of methanol, 44 ml of 1N sodium hydroxide solution were added and hydrolysis was continued for 20 hours at room temperature. The mixture was acidified with hydrochloric acid and then evaporated down under reduced pressure to remove the methanol. The aqueous solution was extracted with ethyl acetate, the combined ethyl acetate extracts were washed with a little water, dried over sodium sulfate and evaporated down and the residue was co-evaporated several times with toluene to give 7.8 g (about 100%) of N-benzyloxycarbonyl-L-prolyl-1-aminocyclopentane-1-carboxylic acid.

2.7 ml of isobutyl chloroformate were added dropwise to 7.7 g of N-benzyloxycarbonyl-L-prolyl-1-amino-cyclopentane-1-carboxylic acid and 2.9 ml of triethyl-amine in 30 ml of dimethylformamide at −10° C., while stirring. After 15 minutes, a suspension of 2.3 g of glycinamide hydrochloride in 20 ml of dimethylformamide and 2.9 ml of triethylamine was added to the resulting solution of the asymmetric acid anhydride, and the mixture was stirred for 1 hour at from −10° to 0° C. and then for 48 hours at room temperature. To work up the mixture, it was taken up in ethyl acetate and the solution was washed successively with 10% strength aqueous citric acid solution, sodium carbonate solution and water, dried over sodium sulfate and evaporated down under reduced pressure.

Purification over silica gel (elution with a 15:1 mixture of dichloromethane and methanol) followed by crystallization from ethyl acetate/toluene gave 5.0 g (75%) of N-benzyloxycarbonyl-L-prolyl-1-aminocyclopent-1-ylcarbonyl-glycinamide.

This was dissolved in 100 ml of methanol, and the solution was hydrogenated in the presence of 0.5 g of palladium on carbon (10%). When the theoretical amount of hydrogen had been absorbed, the mixture was filtered over Celit ®, the filtrate was evaporated down under reduced pressure and the residue was crystallized from isopropanol and ether to give 2.9 g (86%) of L-prolyl-1-aminocyclopent-1-ylcarbonyl-glycinamide of melting point 167°–168° C. (isopropanol/ether).

The following compounds were obtained by a similar method:

10. L-Prolyl-1-aminocycloprop-1-ylcarbonyl-glycinamide (15%), $[\alpha]_D^{20} = -37°$ (c=0.5, methanol);

11. L-Prolyl-1-aminocyclobut-1-ylcarbonyl-glycinamide (40%), $[\alpha]_D^{20} = -39°$ (c=0.5, methanol);
12. L-Prolyl-1-aminocyclohex-1-ylcarbonyl-glycinamide (36%), mp.=143°-146° C. (isopropanol/ether/hexane), $[\alpha]_D^{20} = -36°$ (c=0.6, methanol);
13. L-Prolyl-1-aminocyclohept-1-ylcarbonyl-glycinamide (31%), mp.=170°-174° C. (isopropanol/ether);
14. L-Prolyl-2-aminoindan-2-ylcarbonyl-glycinamide (29%), mp.=178°-181° C. (ethyl acetate), $[\alpha]_D^{20} = -38°$ (c=0.5, methanol).

EXAMPLE 15

L-Prolyl-D-1-aminoindan-1-ylcarbonyl-glycinamide and
L-prolyl-L-1-aminoindan-1-ylcarbonyl-glycinamide 11.4 ml of triethylamine and 26.0 g of the N-hydroxysuccinimide ester of N-benzyloxycarbonyl-L-proline were added to 13.4 g of methyl 1-aminoindane-1-carboxylate in 80 ml of dioxane at 10° C., and the reaction mixture was stirred for 4 hours at this temperature. Thereafter, 15 ml of water were added and the reaction was allowed to continue for 18 hours at room temperature. The mixture was taken up in ethyl acetate, and the organic phase was washed successively with 10% strength aqueous citric acid solution, sodium carbonate solution and water, dried over sodium sulfate and evaporated down under reduced pressure to give 20.5 g (74%) of crude methyl N-benzyloxycarbonyl-L-prolyl-D,L-1-aminoindane-1-carboxylate.

This was dissolved in 300 ml of dioxane, 18.0 ml of 4N sodium hydroxide solution were added and hydrolysis was carried out at room temperature. The mixture was acidified with dilute hydrochloric acid, after which the dioxane was substantially evaporated off under reduced pressure and the residue was taken up in ethyl acetate. The organic phase was extracted exhaustively with potassium bicarbonate solution, the combined aqueous extracts were acidified with hydrochloric acid and the mixture was then extracted with ethyl acetate. The organic phase was dried and then evaporated down under reduced pressure to give 11.0 g (55%) of N-benzyloxycarbonyl-L-prolyl-D,L-1-aminoindane-1-carboxylic acid.

3.5 ml of isobutyl chloroformate were added dropwise to 10.2 g of N-benzyloxycarbonyl-L-prolyl-D,L-1-aminoindane-1-carboxylic acid and 3.8 ml of triethylamine in 30 ml of dimethylformamide at −10° C., while stirring. After 10 minutes, a suspension of 3.0 g of glycinamide hydrochloride in 30 ml of dimethylformamide and 3.8 ml of triethylamine was added to the resulting asymmetric acid anhydride, and the mixture was stirred for 1 hour at from −10° to 0° C. and then for 48 hours at room temperature. To work up the mixture, it was taken up in ethyl acetate and the solution was washed successively with 10% strength aqueous citric acid solution, sodium carbonate solution and water, dried over sodium sulfate and evaporated down under reduced pressure. The residue was chromatographed over a silica gel column (elution with a 20:1 mixture of dichloromethane and methanol). The following two pure isomers were obtained, in order of increasing polarity:
N-benzyloxycarbonyl-L-prolyl-D-1-aminoindan-1-ylcarbonylglycinamide: 3.9 g (34%) and
N-benzyloxycarbonyl-L-prolyl-L-1-aminoindan-1-ylcarbonylglycinamide: 0.8 g (7%).
3.7 g of N-benzyloxycarbonyl-L-prolyl-D-1-aminoindan-1-ylcarbonyl-glycinamide were dissolved in 250 ml of methanol, and the solution was hydrogenated in the presence of 0.5 g of palladium on carbon (10%). After the theoretical amount of hydrogen had been absorbed, the mixture was filtered over Celit ®, the filtrate was evaporated down under reduced pressure, and the residue was crystallized from ethyl acetate/petroleum ether to give 2.1 g (83%) of L-prolyl-D-1-aminoindan-1-ylcarbonylglycinamide (15b), $[\alpha]_D^{20} = -86°$ (c=0.5, methanol).

0.4 g (80%) of L-prolyl-L-1-aminoindan-1-ylcarbonyl-glycinamide (15a), $[\alpha]_D^{20} = 14°$ (c=0.5, methanol), was obtained from 0.7 g of N-benzyloxycarbonyl-L-prolyl-L-1-aminoindan-1-ylcarbonyl-glycinamide by a similar method.

The following compounds were obtained by a similar procedure:

16a. L-Prolyl-L-2-amino(2.2.1)bicyclohept-2-ylcarbonylglycinamide (11%), mp.=233°-238° C. (dichloromethane/petroleum ether), $[\alpha]_D^{20} = -55°$ (c=0.5, methanol);
16b. L-Prolyl-D-2-amino(2.2.1)bicyclohept-2-ylcarbonylglycinamide (26%), mp.=153°-160° C. (dichloromethane/petroleum ether), $[\alpha]_D^{20} = -3°$ (c=0.5, methanol);
7a. L-Prolyl-L-2-methylphenylalanyl-glycinamide (20%), mp.=158°-164° C. (methanol/ether/hexane), $[\alpha]_D^{20} = +48°$ (c=0.5, methanol);
17b. L-Prolyl-D-2-methylphenylalanyl-glycinamide (18%), mp.=184°-186° C. (methanol/ether/hexane), $[\alpha]_D^{20} = -93°$ (c=0.4, methanol);
18a. L-Prolyl-L-2-amino-2-phenylpropionyl-glycinamide (21%), mp.=138°-142° C. (dichloromethane/ether/hexane), $[\alpha]_D^{20} = -15°$ (c=0.5, methanol);
18b. L-Prolyl-D-2-amino-2-phenylpropionyl-glycinamide (24%), mp.=86°-92° C. (dichloromethane/ether/hexane), $[\alpha]_D^{20} = -42°$ (c=0.5, methanol);
19a. L-Prolyl-L-2-amino-2-phenylbutyryl-glycinamide (15%), mp.=151°-158° C. (isopropanol/ether), $[\alpha]_D^{20} = -5°$ (c=0.5, methanol);
19b. L-Prolyl-D-2-amino-2-phenylbutyryl-glycinamide (33%), mp.=174°-175° C. (isopropanol/ether), $[\alpha]_D^{20} = -63°$ (c=0.5, methanol);
20a. L-Prolyl-L-2-amino-2-phenylvaleryl-glycinamide (10%), $[\alpha]_D^{20} = -4°$ (c=0.5, methanol);
20b. L-Prolyl-D-2-amino-2-phenylvaleryl-glycinamide (30%), mp.=138°-141° C. (ether/hexane), $[\alpha]_D^{20} = -65°$ (c=0.5, methanol);
21a. L-Prolyl-L-2-amino-2-(1-naphthyl)-propionyl-glycinamide (10%), mp.=115°-120° C., $[\alpha]_D^{20} = -9°$ (c=0.5, methanol);
21b. L-Prolyl-D-2-amino-2-(1-naphthyl)-propionyl-glycinamide (25%), mp.=113°-120° C., $[\alpha]_D^{20} = -34°$ (c=0.5, methanol).

EXAMPLE 22

The following compounds were obtained by a procedure similar to that described in Example 15, except that the benzyloxycarbonyl protective groups were split off using hydrobromic acid in glacial acetic acid: p0 22a. L-Prolyl-L-2-amino-2-p-bromophenyl-butyryl-glycinamide hydrobromide (10%), mp.=196°-210° C., $[\alpha]_D^{20}=0°$ (c=0.5, methanol) and
22b. L-Prolyl-D-2-amino-2-p-bromophenyl-butyryl-glycinamide hydrobromide (25%), mp.=185°-202°C., $[\alpha]_D^{20} = -51°$ (c=0.5, methanol).
Examples of pharmaceutical formulations:

EXAMPLE A

The following composition was converted to tablets in a conventional manner on a tablet press:
40 mg of the substance from Example 2b
20 mg of corn starch
13.5 mg of gelatine
45 mg of lactose
2.25 mg of Aerosil ® (chemically pure submicroscopic silica)
6.75 mg of potato starch (as a 6% strength paste).

EXAMPLE B

Coated tablets having the following composition were produced in a conventional manner:
20 mg of the substance from Example 2b
60 mg of core material
60 mg of sugar-coating material.

The core comprised 9 parts of corn starch, 3 parts of lactose and 1 part of Luviskol ® VA 64 (60:40 vinylpyrrolidone/vinyl acetate copolymer; cf. Pharm. Ind. 1962, 586). The sugar-coating material comprised 5 parts of sucrose, 2 parts of corn starch, 2 parts of calcium carbonate and 1 part of talc. The coated tablets thus obtained were then provided with a shell resistant to gastric juices.

We claim:

1. A compound of the formula I $$X-NH-CR^2R^3-CO-NH-CH_2-CO-R^1 \qquad I$$

where $R_1$ is $NH_2$, $R_2$ is phenyl or naphthyl and $R_3$ is $C_1$-$C_5$-alkyl, or $R_2$ and $R_3$ form a cycloalkyl of 3 to 6 carbon atoms, and X is pyrrol-2-yl carbonyl, L-pyrrolidin-2-ylcarbonyl, L-4,5-dehydropyrrolidin-2-ylcarbonyl, and its salts with physiologically tolerated acids.

2. A therapeutic composition for treating depression comprising a pharmaceutical excipient and from 0.1 to 99% by weight of a compound I as described in claim 1 as the active compound.

3. The method of treating depression in a patient suffering therefrom, which comprises administering to the patient an antidepressive effective amount of a compound according to claim 1.

4. The method of claim 3, wherein a daily dose of from 0.1 to 100 mg/kg of body weight of the compound is orally administered to the patient.

5. The method of claim 3, wherein a daily dose of from 0.01 to 10 mg/kg of body weight of the compound is parenterally administered to the patient.

6. A compound of the formula I as described in claim 1, wherein X is L-pyrrolidin-2-ylcarbonyl.

* * * * *

UNITED STATES PATENT AND TRADEMARK OFFICE
CERTIFICATE OF CORRECTION

PATENT NO. : 4,610,817

DATED : September 9, 1986

INVENTOR(S) : Hans Peter ALBRECHT et al.

It is certified that error appears in the above-identified patent and that said Letters Patent is hereby corrected as shown below:

Please add the following:

-- [30] Foreign Application Priority Data

July 14, 1982 [DE] Fed. Rep. of Germany... 3226241 --

Signed and Sealed this

Twenty-fifth Day of November, 1986

*Attest:*

DONALD J. QUIGG

*Attesting Officer*      *Commissioner of Patents and Trademarks*